United States Patent
Polsinelli et al.

(10) Patent No.: US 7,414,254 B2
(45) Date of Patent: *Aug. 19, 2008

(54) TUNGSTEN PIG FOR RADIO-PHARMACEUTICALS

(75) Inventors: Perry Polsinelli, Suwanee, GA (US); Jeff D. D'Alonzo, Dacula, GA (US); Steven B. West, Ball Ground, GA (US)

(73) Assignee: United Pharmacy Partners, Inc., Suwanee, GA (US)

( * ) Notice: Subject to any disclaimer, the term of this patent is extended or adjusted under 35 U.S.C. 154(b) by 672 days.

This patent is subject to a terminal disclaimer.

(21) Appl. No.: 11/168,813

(22) Filed: Jun. 28, 2005

(65) Prior Publication Data

US 2006/0293552 A1    Dec. 28, 2006

(51) Int. Cl.
*G21F 5/00* (2006.01)
*G21F 5/018* (2006.01)
*A61N 5/00* (2006.01)

(52) U.S. Cl. .............. 250/507.1; 250/506.1; 250/515.1
(58) Field of Classification Search .............. 250/507.1, 250/506.1, 515.1
See application file for complete search history.

(56) References Cited

U.S. PATENT DOCUMENTS

| | | | |
|---|---|---|---|
| 5,828,073 A | 10/1998 | Zhu et al. | |
| 5,927,351 A | 7/1999 | Zhu et al. | |
| 6,425,174 B1 * | 7/2002 | Reich | ............ 29/469 |
| 6,576,918 B1 | 6/2003 | Fu et al. | |
| 6,586,758 B2 | 7/2003 | Martin | |
| 6,717,163 B2 * | 4/2004 | Zens | ......... 250/515.1 |
| 6,722,499 B2 | 4/2004 | Reich | |
| 6,822,253 B1 | 11/2004 | Martin et al. | |
| 7,086,133 B2 | 8/2006 | Reich | |
| 7,307,265 B2 * | 12/2007 | Polsinelli et al. | ......... 250/507.1 |
| 2005/0198800 A1 | 9/2005 | Reich | |

* cited by examiner

*Primary Examiner*—Nikita Wells
(74) *Attorney, Agent, or Firm*—Bockop & Associates, LLC; Bryan W. Bockop

(57) ABSTRACT

A radio-pharmaceutical transport system includes a pig and a disposable plastic insert. Together, the pig and the disposable plastic insert provide a mechanism for transporting a syringe containing a dose of a radio-pharmaceutical composition. The pig includes a tungsten cylinder that defines an elongated cavity therein that is substantially coaxial with the tungsten cylinder. The cavity is of sufficient size to receive therein a syringe. The tungsten cylinder has a thickness sufficient to shield users from a PET radio-pharmaceutical without requiring additional shielding. The disposable plastic insert is disposed within the cavity and includes an elongated plastic envelope.

21 Claims, 3 Drawing Sheets

TUNGSTEN PIG FOR RADIO-PHARMACEUTICALS

BACKGROUND OF THE INVENTION

1. Field of the Invention

The present invention relates to medical devices and, more specifically, to a device for transporting radio-pharmaceuticals used in positron emission tomography.

2. Description of the Prior Art

Positron emission tomography (PET) imaging is a diagnostic examination that involves acquiring physiologic images based on the detection of positron radiation. Positrons are particles emitted from radioactive substances. The radioactive substances used are injected into a patient and positrons from the radioactive substance are detected and imaged by a PET scanner. The resulting images are used to evaluate a variety of diseases.

Pharmaceutical compositions used in PET scans are administered in liquid form by injection into the patient. Radio-pharmacists typically calculate a unit dose based on the amount of decay that a dose will undergo during transport to the hospital at which the dose will be administered. In preparing the dose, the radio-pharmacist places the dose into a syringe and then places the syringe into a "pig" that shields those handling the dose from the radioactive contents of the syringe. The pig is then transported to the hospital for administration to a patient.

With many types of radio-pharmaceuticals, a lead pig is sufficient to shield those handling the dose. However, for radio-pharmaceuticals designed for PET scans, a typical lead-shielded pig does not provide sufficient protection by itself. To compensate, existing PET radio-pharmaceutical transport systems require an extra level of shielding. This is accomplished by providing a secondary shielded case for the pig. Such a shielded case includes lead shielding about a cylindrical opening into which the pig fits.

Existing PET radio-pharmaceutical pigs tend to need to be replaced on a regular basis. This is because the shielding quality of lead breaks down in the presence of PET pharmaceutical radiation. Thus, the cost is increased. Also, there is a danger of insufficient protection if a radio-pharmacist continues to use a pig past its designed life span.

Because most pigs are roughly cylindrical in shape, rolling of such pigs is a problem. If a pig is allowed to roll, it could roll off of the surface on which it is placed and fall, causing injury, destroying the dose of the radio-pharmaceutical composition contained therein, or both. Some existing pigs include a flat surface milled into the outer surface of the pig. The milling is done by removing several exterior chords of the cylinder forming the pig, thereby forming flat surfaces. Also, several small evenly-spaced bumps may be added to the exterior surface of the pig. Both of these methods of preventing rolling may be satisfactory for ordinary conditions, but they do not provide a sufficient anti-roll capability in situations in which a pig is accidentally bumped with considerable force. Furthermore, most pigs include two sections that must be separated when accessing the syringe inside. However, many existing pigs usually include anti-roll texturing on only one section. Thus, if the section without the anti-roll texturing is placed on a table, it may roll off and cause injury.

Typical radio-pharmaceutical pigs have an inner chamber into which a filled syringe is placed. A plastic liner is frequently employed to prevent spillage from the syringe from accumulating inside the pig. Such a liner is typically made from rigid plastic and used only once. Because the liner is rigid, it takes up a considerable amount of space to store and to dispose of.

Therefore, it would be desirable for a radio-pharmaceutical pig to be capable of providing sufficient shielding for a dose of at PET radio-pharmaceutical, without requiring secondary shielding.

It would also be desirable for a radio-pharmaceutical pig not to require frequent replacement.

It would also be desirable for a radio-pharmaceutical pig to have an anti-roll feature that positively prevents rolling of the pig even when subjected to a substantial force.

It would also be desirable for a radio-pharmaceutical pig insert to be easily storable and easily disposable.

SUMMARY OF THE INVENTION

The disadvantages of the prior art are overcome by the present invention which, in one aspect, is a radio-pharmaceutical transport system that includes a pig and a disposable plastic insert. Together, the pig and the disposable plastic insert provide a mechanism for transporting a syringe containing a dose of a radio-pharmaceutical composition.

The pig includes a tungsten cylinder that defines an elongated cavity therein that is substantially coaxial with the tungsten cylinder. The cavity is of sufficient size to receive therein a syringe. The tungsten cylinder has a thickness sufficient to shield users from a PET radio-pharmaceutical without requiring additional shielding. The tungsten cylinder includes a first elongated member and a second elongated member. The first elongated member terminates in a first engagement surface and an opposite first distal end. The second elongated member terminates in a second engagement surface, that is complimentary to the first engagement surface, and an opposite second distal end. The first engagement surface defines a recess having a shape that facilitates holding a finger grip of a syringe. A first anti-roll member extends outwardly from the first distal end and a second anti-roll member extends outwardly from the second distal end.

The disposable plastic insert is disposed within the cavity and includes an elongated plastic envelope. The disposable plastic insert includes a first sheet and an oppositely-disposed second sheet. The first sheet is sealed to the second sheet along three sides and opens to a top side. The disposable plastic insert defining passage therein. The passage is of sufficient size to allow a syringe to fit therein. A first adhesive tab is disposed on the first sheet adjacent the top side and a second adhesive tab is disposed on the second sheet adjacent the top side. The first adhesive tab and the second adhesive tab include a peel-off cover that may be peeled off to allow exposure of the adhesive tabs so as to facilitate sealing the top side.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
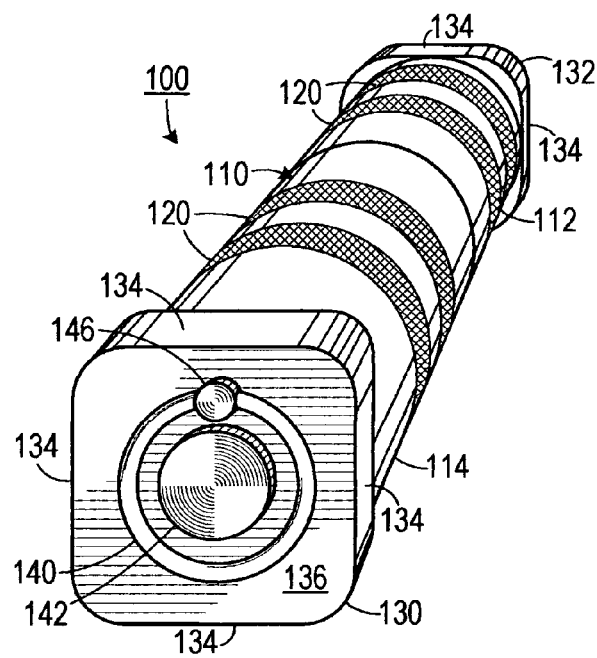
FIG. 1 is a top perspective view of one illustrative embodiment of the invention.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

As used herein, "plastic" means capable of being deformed without rupture and a "plastic material" includes materials that are deformable. Plastic materials, as used herein, include, but are not limited to, synthetic polymer materials, natural latex materials, thin metal sheets and combinations thereof. It will be readily understood that many other materials, not specifically listed herein, will meet the criteria for being a plastic within the scope of the present invention.

As shown in FIG. 1, one illustrative embodiment of a radio-pharmaceutical pig 100 includes a tungsten cylinder 110 having a first elongated member 112 and a second elongated member 114. The outer surface of the first elongated member 112 and the second elongated member 114 includes a rough textured portion 120 that facilitates gripping of the pig 100 by a user. Typically, the pig 100 is formed from titanium stock and formed on a metal lathe using conventional methods.

Figure 2A:
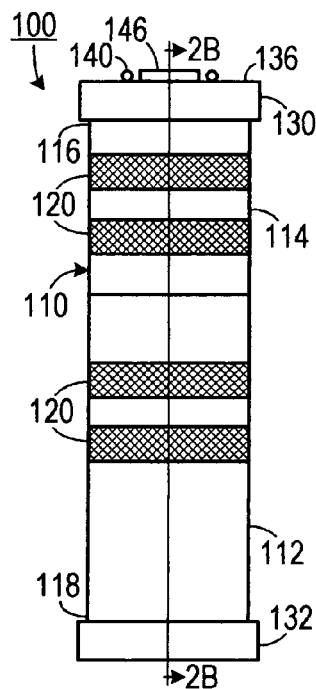
FIG. 2A is an elevational view of one embodiment.
Figure 2B:
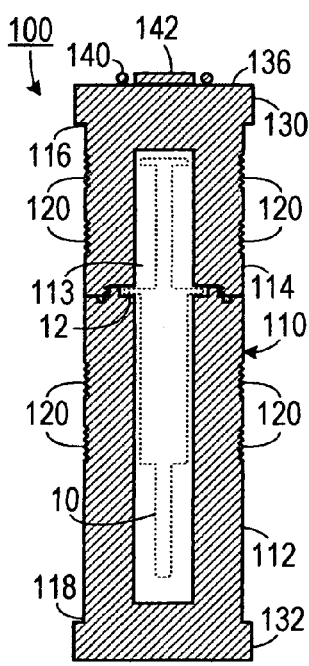
FIG. 2B is a cross-sectional view of the embodiment shown in FIG. 2A, taken along line 2B-2B.
Figure 2C:
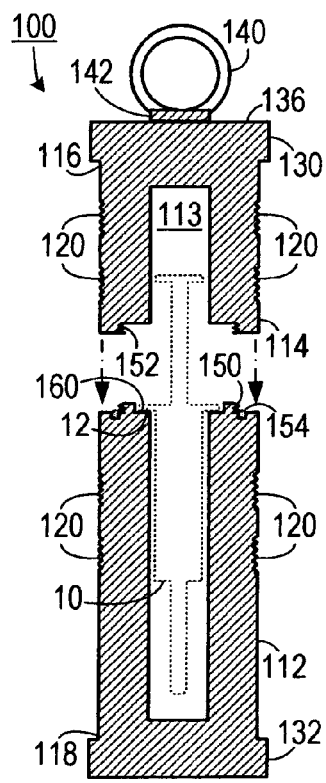
FIG. 2C is an expanded cross-sectional view of the embodiment shown in FIG. 2B.

As shown in FIGS. 2A-2C, the first elongated member 112 terminates in a first engagement surface 150 and an opposite first distal end 118, the second elongated member 114 terminating in a second engagement surface 152 that is complimentary to the first engagement surface 150 and an opposite second distal end 116. The pig 100 defines an elongated cavity 113 therein that is substantially coaxial with the tungsten cylinder 110. The cavity 113 is of sufficient size to receive a syringe 10 therein. The tungsten cylinder 110 is thick enough to shield users from a PET radio-pharmaceutical without requiring additional shielding. The actual thickness may be calculated easily by referring to standard radiological shielding tables and depends on the type and amount of radio-pharmaceutical being used.

A recess 160 may be milled into either the first engagement surface 150 or the second engagement surface 152 (or both) to receive the finger grip tabs of the syringe 10, thereby preventing the syringe 10 from rocking during transport. An O-ring 154 may be embedded in one of the engagement surfaces 150 or 152 to prevent leakage from the pig 100.

Returning to FIG. 1, a first anti-roll member 132 extends outwardly from the first distal end 118 and a second anti-roll member 130 extends outwardly from the second distal end 116. The first anti-roll member 132 and the second anti-roll member 130 each include at least three (and in the embodiment shown, four) flat surfaces 134 that inhibit rolling. Including an anti-roll member 132 and 130 on each of the first elongated member 112 and the second elongated member 114, ensures that neither member will roll if left unattended on a flat surface. This may be a substantial advantage, given that each elongated member 112 and 114 will likely be quite heavy due to the thickness of the tungsten employed.

The second distal end 116 is supplied with a lifting ring 140 that facilitates lifting of the pig 100 out of any carrying container (not shown) used to transport the pig 100. The lifting ring may be affixed to the top surface 136 of the pig 100 with an attachment 146 and a spacing plug 142 may be affixed to the top surface 136 inside the ring 140 when the ring 140 is in the down position.

Figure 2D:
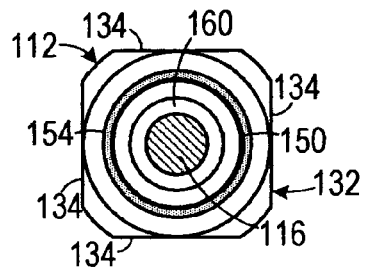
FIG. 2D is a bottom plan view of the embodiment shown in FIG. 2A.
Figure 2E:
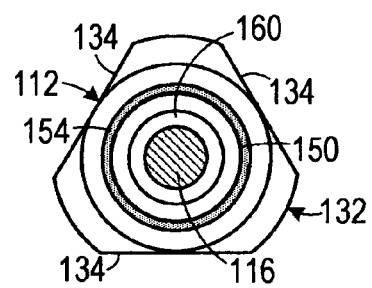
FIG. 2E is a bottom plan view of an alternate embodiment of the invention.

As shown in FIG. 2D, the anti-roll members 132 are blocks of titanium that could include four flat sides 134, or, as shown in FIG. 2E, only three flat sides 134, or even more than four flat sides 134, so long as the flat side 134 has dimensions sufficient to prevent rolling. The anti-roll members 132 may be formed from the same titanium stock as the rest of the pig 100.

Figure 2F:
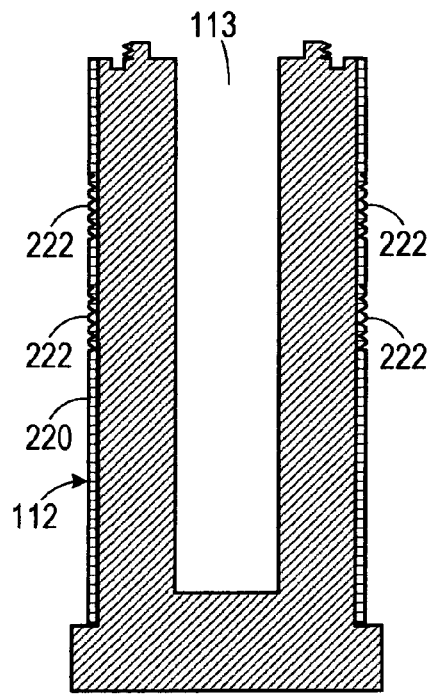
FIG. 2F is a cross sectional view of a detail of the embodiment shown in FIG. 2B.

As shown in FIG. 2F, a stainless steel sleeve 220 may disposed about a portion of the tungsten cylinder 110. The textured portion 222 may be cut into the stainless steel sleeve 220 and may include diamond patterned scoring.

Figure 3:
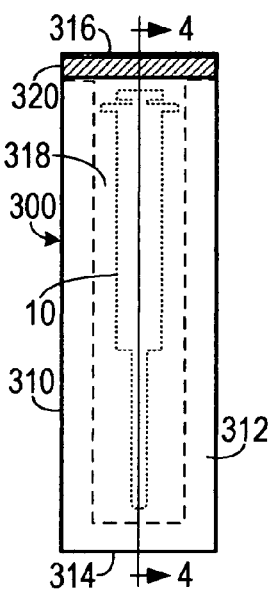
FIG. 3 is a plan view of a plastic insert.
Figures 4A, 4B:
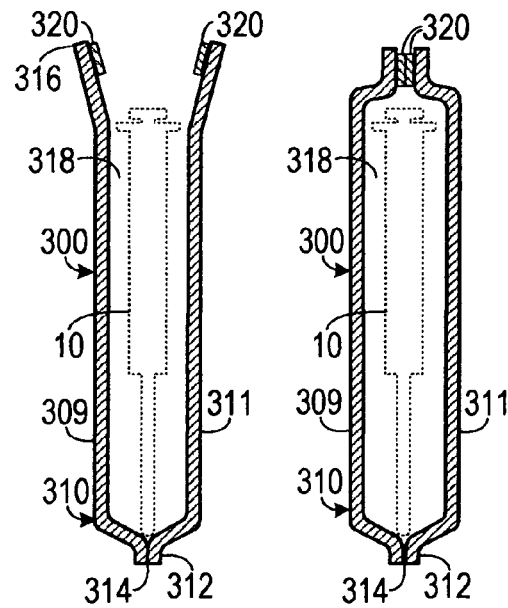
FIG. 4A is a cross-sectional view of the insert shown in FIG. 3, taken along line 4-4.
FIG. 4B is a second cross-sectional view of the insert shown in FIG. 3, taken along line 4-4.
Figure 5:
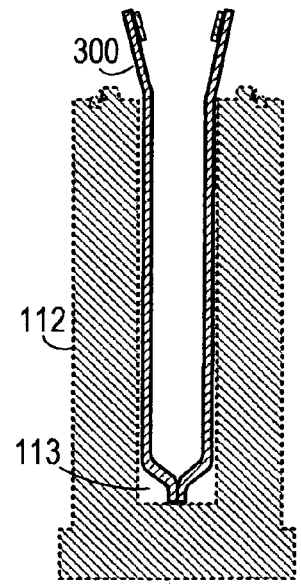
FIG. 5 is a cross-sectional view of an insert disposed within a pig.

As shown in FIGS. 3-5, a disposable plastic insert 300 is disposed within the cavity 113 to prevent leakage of radio-pharmaceutical materials into the cavity 113. Each insert 300 includes an elongated plastic envelope 310 made from a first plastic sheet 309 and an oppositely-disposed second plastic sheet 311 that are sealed together along a sealing surface 312 (through thermal sealing, for example) and that open to a top side 316, thereby defining passage therein 318. The passage is of sufficient size to allow a syringe 10 to fit therein. The disposable plastic insert 300 could be made of materials including polyethylene and polyvinyl chloride, but should be thick enough to resist punctures from any exposed needles placed into the insert 300.

A first adhesive tab 320 is placed on the first sheet 309 adjacent the top side 316 and a second adhesive tab 320 is placed on the second sheet 311 adjacent the top side 316. The first adhesive tab 320 and the second adhesive tab 320 each include a peel-off cover that may be peeled off to allow exposure of the adhesive tabs 320 so as to facilitate sealing the top side (as shown in FIG. 4B). This facilitates easy sealing of the syringe 10 for disposal after use.

Figure 6:
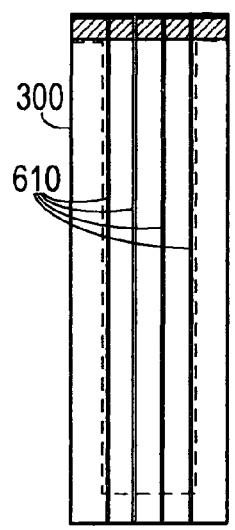
FIG. 6 is a plan view of a plastic insert including stiffening ribs.

As shown in FIG. 6, the disposable plastic insert 300 may also include a plurality of elongated rib structures 610 embedded in one of the plastic sheets 310 and 311 to provide structural support to the plastic insert 300. The elongated ridge structures 610 could include wires embedded in one of the plastic sheets 310 and 311, or could be thickened plastic that is molded into the plastic sheets 310 and 311 using commonly-known plastic sheet forming methods.

Figure 7:
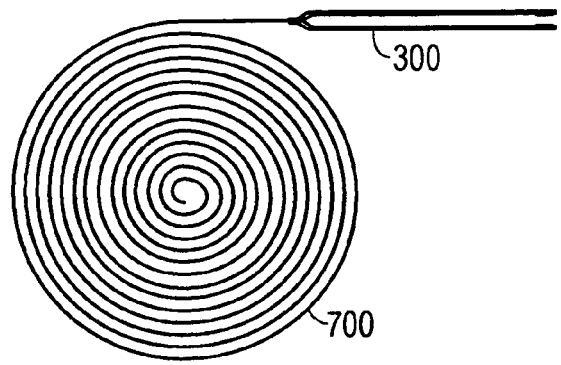
FIG. 7 is a side view of a roll of plastic inserts.
Figure 8:
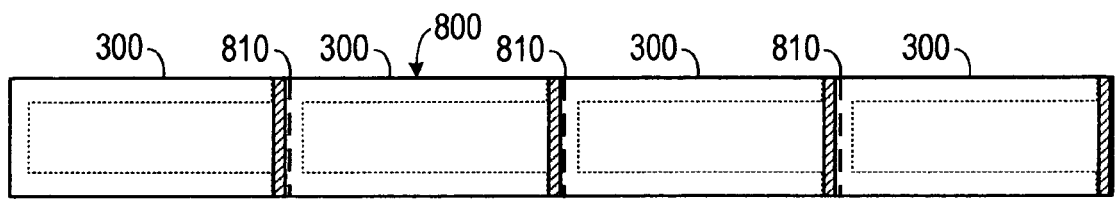
FIG. 8 is a plan view of a strip of plastic inserts.

As shown in FIG. 7, because the inserts 300 are flexible, a plurality of inserts 300 may be formed continuously and stored in the form of a roll 700. This facilitates easy manufacturing and storage of the inserts. As shown in FIG. 8, when the inserts are formed as a continuous strip 800, a serration 810 may be cut in the sealed portion between each successive insert 300 in the strip 800 to facilitate separation of the inserts 300.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A radio-pharmaceutical transport system, comprising:
   a. a pig, including
      i. a tungsten cylinder defining an elongated cavity therein that is substantially coaxial with the tungsten cylinder, the cavity being of sufficient size to receive therein at least a portion of a syringe, the tungsten cylinder having a thickness sufficient to shield users from a PET radio-pharmaceutical without requiring additional shielding, the tungsten cylinder including a first elongated member and a second elongated member, the first elongated member terminating in a first engagement surface and an opposite first distal end, the second elongated member terminating in a second engagement surface, that is complimentary to the first engagement surface, and an opposite second distal end, the first engagement surface defining a recess having a shape that facilitates holding a finger grip of a syringe;
      ii. a first anti-roll member extending outwardly from the first distal end; and
      iii. a second anti-roll member extending outwardly from the second distal end; and
   b. a disposable plastic insert disposed within the cavity, including:
      i. an elongated plastic envelope including a first sheet and an oppositely-disposed second sheet, the first sheet sealed to the second sheet along three sides, opening to a top side and defining passage therein, the passage being of sufficient size to allow a syringe to fit therein; and
      ii. a first adhesive tab disposed on the first sheet adjacent the top side and a second adhesive tab disposed on the second sheet adjacent the top side, the first adhesive tab and the second adhesive tab including a peel-off cover that may be peeled off to allow exposure of the adhesive tabs so as to facilitate sealing the top side.

2. The radio-pharmaceutical transport system of claim 1, wherein the first elongated member and the second elongated member each having an exterior surface that includes a textured portion that facilitates gripping by a user.

3. The radio-pharmaceutical transport system of claim 2, further comprising a stainless steel sleeve disposed about a portion of the tungsten cylinder into which is cut the textured portion.

4. The radio-pharmaceutical transport system of claim 2, wherein the textured portion comprises diamond patterned scoring.

5. The radio-pharmaceutical transport system of claim 1, wherein the first anti-roll member and the second anti-roll member each comprise a block that extends outwardly from the tungsten cylinder, the block having at least three substantially flat sides.

6. The radio-pharmaceutical transport system of claim 5, wherein the block has four substantially flat sides.

7. The radio-pharmaceutical transport system of claim 1, wherein the disposable plastic insert comprises at least one elongated rib structure embedded in at least one of the first plastic sheet and the second plastic sheet so as to provide structural support to the plastic insert.

8. The radio-pharmaceutical transport system of claim 1, wherein the disposable plastic insert comprises a material selected from a group consisting essentially of polyethylene and polyvinyl chloride.

9. A radio-pharmaceutical pig, comprising:
   a. a tungsten cylinder defining an elongated cavity therein that is substantially coaxial with the tungsten cylinder, the cavity being of sufficient size to receive therein a syringe, the tungsten cylinder having a thickness sufficient to shield users from a PET radio-pharmaceutical without requiring additional shielding, the tungsten cylinder including a first elongated member and a second elongated member, the first elongated member terminating in a first engagement surface and an opposite first distal end, the second elongated member terminating in a second engagement surface that is complimentary to the first engagement surface and an opposite second distal end;
   b. a first anti-roll member extending outwardly from the first distal end; and
   c. a second anti-roll member extending outwardly from the second distal end.

10. The radio-pharmaceutical pig of claim 9, wherein the first elongated member and the second elongated member each having an exterior surface that includes a textured portion that facilitates gripping by a user.

11. The radio-pharmaceutical pig of claim 10, further comprising a stainless steel sleeve disposed about a portion of the tungsten cylinder into which is cut the textured portion.

12. The radio-pharmaceutical pig of claim 10, wherein the textured portion comprises diamond patterned scoring.

13. The radio-pharmaceutical pig of claim 9, wherein the first engagement surface defines a recess having a shape that facilitates holding a finger grip of a syringe.

14. The radio-pharmaceutical pig of claim 9, wherein the first anti-roll member and the second anti-roll member each comprise a block that extends outwardly from the tungsten cylinder, the block having at least three substantially flat sides.

15. The radio-pharmaceutical pig of claim 14, wherein the block has four substantially flat sides.

16. The radio-pharmaceutical pig of claim 9, further comprising a disposable plastic insert disposed within the cavity, the disposable plastic insert comprising:
   a. an elongated plastic envelope including a first sheet and an oppositely-disposed second sheet, the first sheet sealed to the second sheet along three sides, opening to a top side and defining passage therein, the passage being of sufficient size to allow a syringe to fit therein; and
   b. a first adhesive tab disposed on the first sheet adjacent the top side and a second adhesive tab disposed on the second sheet adjacent the top side, the first adhesive tab and the second adhesive tab including a peel-off cover that may be peeled off to allow exposure of the adhesive tabs so as to facilitate sealing the top side.

17. The radio-pharmaceutical pig of claim 16, wherein the disposable plastic insert comprises at least one elongated rib structure embedded in at least one of the first plastic sheet and the second plastic sheet so as to provide structural support to the plastic insert.

18. An insert for use with a radio-pharmaceutical pig, comprising:
  a. an elongated plastic envelope including a first sheet and an oppositely-disposed second sheet, the first sheet sealed to the second sheet along three sides, opening to a top side and defining passage therein, the passage being of sufficient size to allow a syringe to fit therein, the elongated plastic envelope having a shape so as to fit into a cavity defined by a radio-pharmaceutical pig, the first sheet and the second sheet being of sufficient thickness so as to resist puncturing by a syringe needle; and
  b. a first adhesive tab disposed on the first sheet adjacent the top side and a second adhesive tab disposed on the second sheet adjacent the top side, the first adhesive tab and the second adhesive tab including a peel-off cover that may be peeled off to allow exposure of the adhesive tabs so as to facilitate sealing the top side.

19. The insert for use with a radio-pharmaceutical pig of claim 18, wherein the disposable plastic insert comprises at least one elongated rib structure embedded in at least one of the first plastic sheet and the second plastic sheet so as to provide structural support to the plastic insert.

20. The insert for use with a radio-pharmaceutical pig of claim 18, wherein the insert is one of a plurality of inserts arranged as a strip of inserts, a serration defined between each successive insert in the strip of inserts to facilitate separation of the inserts.

21. The insert for use with a radio-pharmaceutical pig of claim 18, wherein the disposable plastic insert comprises a material selected from a group consisting essentially of: polyethylene and polyvinyl chloride.

* * * * *